US012514726B1

(12) United States Patent
Anderson et al.

(10) Patent No.: US 12,514,726 B1
(45) Date of Patent: Jan. 6, 2026

(54) HEMORRHOID TREATMENT DEVICE, SYSTEM AND METHOD

(71) Applicants: Brent Anderson, Gilroy, CA (US); Cortland Bohacek, Woodside, CA (US)

(72) Inventors: Brent Anderson, Gilroy, CA (US); Cortland Bohacek, Woodside, CA (US)

( * ) Notice: Subject to any disclaimer, the term of this patent is extended or adjusted under 35 U.S.C. 154(b) by 15 days.

(21) Appl. No.: 18/594,741

(22) Filed: Mar. 4, 2024

Related U.S. Application Data

(60) Provisional application No. 63/449,343, filed on Mar. 2, 2023.

(51) Int. Cl.
*A61F 5/00* (2006.01)

(52) U.S. Cl.
CPC .................................. *A61F 5/0093* (2013.01)

(58) Field of Classification Search
CPC ........... A61B 5/00; A61B 5/0093; A61B 5/08; A61B 17/0057
See application file for complete search history.

(56) References Cited

U.S. PATENT DOCUMENTS 4,331,151 A * 5/1982 Golden ..................... A61F 7/12 607/105
2017/0105827 A1* 4/2017 Shalon ...................... A61F 5/48

* cited by examiner

*Primary Examiner* — Vi X Nguyen
(74) *Attorney, Agent, or Firm* — Nyemaster Goode P.C.

(57) ABSTRACT

A hemorrhoid treatment device for the treatment of hemorrhoids in a human that includes an elongated upper portion having a top edge defining a hemorrhoid treatment liquid receiving opening, an elongated upper portion, interior facing surface, and an elongated upper portion, exterior facing surface; a base portion having a hemorrhoid treatment liquid outlet, a base portion, interior facing surface, and a base portion, exterior facing surface; a curved midsection spaced between the elongated upper portion and the base portion having a curved section, interior-facing surface and a curved section, exterior facing surface. The base portion, the curved midsection, and the elongated upper portion, collectively form the hemorrhoid treatment device. The elongated upper portion, interior facing surface aligns with the curved section, interior facing surface and the curved section, interior facing surface aligns with the base portion, interior-facing surface.

20 Claims, 14 Drawing Sheets

HEMORRHOID TREATMENT DEVICE, SYSTEM AND METHOD

CROSS-REFERENCE TO RELATED APPLICATION

This application claims the benefit of priority to U.S. Provisional Patent Application No. 63/449,343, filed Mar. 2, 2023, entitled "HEMORRHOID TREATMENT DEVICE, SYSTEM AND METHOD," the entire disclosure of which is incorporated herein by reference in its entirety.

BACKGROUND

Hemorrhoids, also called piles, are swollen veins in a person's anus and/or lower rectum, similar to varicose veins. Hemorrhoids can develop inside the rectum (internal hemorrhoids) or under the skin around the anus (external hemorrhoids). Nearly three out of four adults will have hemorrhoids from time to time. Hemorrhoids have a number of causes, but often the cause is unknown.

Hemorrhoids are treated with various methods. Rectal insertion devices, either to cool the afflicted areas or to allow surgical tools to reach inside the body cavity, are commonly used to treat hemorrhoids. Another class of devices pushes tissue that rubs against hemorrhoids with the intended goal of relieving pressure and the resultant pain. Less invasive procedures have been developed, including anorectal medicines. While creams are available, there are water activated medicines that are utilized by putting the prescribed amount into a container, such as a bathtub or toilet 10 (FIG. 1), and immersing the anal region into the water containing bowl 12. The hemorrhoids are then exposed to the medicine saturated water. Unfortunately, these methods are difficult to implement and treat only the effected hemorrhoid containing area of the body with the treatment. It is often very difficult to hold one's own weight for a period of time with one small segment of the body submersed in the water to treat the hemorrhoid(s). As a result, often one must completely sit within the water container or toilet to obtain proper treatment, which is typically recommended to be done 2-3 times a day for 5-15 minutes per day. This is obviously extremely uncomfortable and for most people difficult to stand up from after treatment. This is especially true of older people who are often the ones in most need of this type of treatment.

SUMMARY

The present disclosure generally relates to apparatuses and methods for treatment of hemorrhoids. More particularly, the present disclosure relates to a lavage device to apply treatment directly to hemorrhoids.

One aspect of the present invention includes a lavage device having a left and right-side wall that anatomically curves as to fit against the user's buttocks, a back portion connected to each side wall that curves forward and terminates with a lip, and forming trough shape with the side walls that is L-shaped. Inside the trough is a horizontal groove, which is used to interface with an attachment part to extend the length of the device. A pair of generally parallel side ridges to assist in securing the device to the user's skin run along both the right and the left-side walls. A handle is attached to the back portion of the device. The handle has a distal edge that is horizontally straight and a proximal edge that meets the distal edge at a right angle and extends downward and meets curvilinearly with the back portion.

The lavage device also has a top edge with a horseshoe shaped cross section, forming an open end to the trough for water entry.

Another aspect of the present invention includes an extension device for attachment to the lavage device that increases its length and including an outer portion with the same horizontal cross section as the lavage device and an inner portion for interfacing with the lavage device. An extension handle is engaged to the back portion of the lavage device in such a way as to enable a grip to attach to the lavage device handle. The inner portion includes an outwardly facing ridge to fit into the grooves of the lavage device, and the outer portion includes an extension groove as to allow another such extension to interface with it. Any number of extensions can be added unto the lavage device enabling it to be customized to fit to the size of the user.

Yet another aspect of the present invention includes a method for using the device to apply treatment to the user's hemorrhoids. The device is filled with the treatment, inserted in between the buttocks so that the top end of the device is oriented outwards and upwards so that water may flow into the open end. The user stands in the shower with their back oriented towards the incoming stream of water. The medicine will be activated by the water flowing into the device and the hemorrhoids are suitably exposed. The method offers a convenient alternative to those in the prior art.

Another aspect of the present disclosure is generally directed a hemorrhoid treatment device for the treatment of hemorrhoids in a human that includes an elongated upper portion having a top edge defining a hemorrhoid treatment liquid receiving opening, an elongated upper portion, interior facing surface, and an elongated upper portion, exterior facing surface; a base portion having a hemorrhoid treatment liquid outlet, a base portion, interior facing surface, and a base portion, exterior facing surface; a curved midsection spaced between the elongated upper portion and the base portion having a curved section, interior-facing surface and a curved section, exterior facing surface. The base portion, the curved midsection, and the elongated upper portion, collectively form the hemorrhoid treatment device. The elongated upper portion, interior facing surface aligns with the curved section, interior facing surface and the curved section, interior facing surface aligns with the base portion, interior-facing surface. The hemorrhoid treatment device includes: a left-side wall having a left-side, human skin-engaging portion and a left-side, rear wall engaging portion on the opposite side of the left-side wall of the left-side, human skin-engaging portion; a right-side wall having a right-side skin-engaging portion and a right-side, rear wall engaging portion opposite the right-side skin-engaging portion; and a back wall extending from the top edge to a back wall bottom portion wherein the back wall is interconnected with the left-side wall and the right-side wall. The right-side, skin-engaging portion and the left-side, skin-engaging portion define a front gap distance that is smaller than the width of the back wall. The hemorrhoid treatment liquid outlet may further include a spout on an end of the base portion distal the curved portion where the spout may have a downwardly facing lip.

Yet another aspect of the present disclosure is generally directed toward a hemorrhoid treatment kit for the treatment of hemorrhoids in a human. The hemorrhoid treatment kit typically includes a hemorrhoid treatment device and at least one extension bracket to optionally lengthen the hemorrhoid treatment device. The hemorrhoid treatment device may include: an elongated upper portion having a top edge defining a hemorrhoid treatment liquid receiving opening, an elongated upper portion, interior facing surface, and an elongated upper portion, exterior facing surface; a base portion having a hemorrhoid treatment liquid outlet, a base portion, interior facing surface, and a base portion, exterior facing surface; a curved midsection spaced between the elongated upper portion and the base portion having a curved section, interior-facing surface and a curved section, exterior facing surface. The base portion, the curved midsection, and the elongated upper portion, collectively form the hemorrhoid treatment device. The elongated upper portion, interior facing surface aligns with the curved section, interior facing surface; the curved section, interior facing surface aligns with the base portion, interior-facing surface; the upper portion, exterior facing surface aligns with the curved section, interior facing surface; and the curved section, interior facing surface aligns with the base portion, interior-facing surface. The hemorrhoid treatment device typically includes: a left-side wall having a left-side, human skin-engaging portion and a left-side, rear wall engaging portion on the opposite side of the left-side wall of the left-side, human skin-engaging portion; a right-side wall having a right-side skin-engaging portion and a right-side, rear wall engaging portion opposite the right-side skin-engaging portion; and a back wall extending from the top edge to a back wall bottom portion, where the back wall is interconnected with the left-side wall and the right-side wall. The right-side, skin-engaging portion and the left-side, skin-engaging portion define a front gap distance that is smaller than the width of the back wall. The planar handle is typically engaged with the back wall and has a handle top edge in the same or substantially in the same plane as a plane defined by the top edge of the elongated upper portion of the hemorrhoid treatment device. The at least one extension bracket typically includes: a main bracket section having an extension bracket upper portion with an exterior surface that faces the exterior of the main bracket section and an interior surface that faces the interior of the main bracket section wherein the interior surface of the main bracket section has a horizontal bracket channel thereon; an extension bracket lower section interior surface; and wherein the main bracket section of the extension bracket has an at least substantially similar cross-sectional shape as the upper portion of the hemorrhoid treatment device; a downward facing, hemorrhoid treatment device engaging projection extending downward from the main bracket section and having an interior facing side and an exterior facing side having a lateral extension configured to frictionally fit within and engage the horizontal groove on the elongated upper portion of the hemorrhoid treatment device when the extension bracket is engaged with the hemorrhoid treatment device; and an extension bracket attachment fin engaged with the main bracket section and extending rearwardly away from the main bracket section wherein the extension bracket attachment fin includes a planar fin section that aligns with the handle main portion when the extension bracket and the hemorrhoid treatment device are engaged with one another; and a downwardly facing u-shaped retainer having a downwardly facing channel that receives the handle top edge within it when the extension bracket and the hemorrhoid treatment device are engaged with one another, a left side pair of bracket ridges that align with the left-side wall pair of ridges when the extension bracket and the hemorrhoid treatment device are engaged with one another and a right side pair of bracket ridges located opposite the left side pair of bracket ridges that align with the right-side wall pair of ridges when the extension bracket and the hemorrhoid treatment device are engaged with one another and wherein the exterior surface of the main bracket section and an exterior surface of the elongated upper portion align with one another when the extension bracket and the hemorrhoid treatment device are engaged with one another.

Another aspect of the present disclosure is generally directed to a method of treating a user's hemorrhoids using a main hemorrhoid treatment device that includes the steps of: while in a shower or under another supply of running water delivered from above a user's waist level, grasping a handle of a hemorrhoid treatment device for the treatment of hemorrhoids in a human that includes: an elongated upper portion having a top edge defining a hemorrhoid treatment liquid receiving opening, an elongated upper portion, interior facing surface, and an elongated upper portion, exterior facing surface; a base portion having a hemorrhoid treatment liquid outlet, a base portion, interior facing surface, and a base portion, exterior facing surface; and a curved midsection spaced between the elongated upper portion and the base portion having a curved section, interior-facing surface and a curved section, exterior facing surface. The base portion, the curved midsection, and the elongated upper portion, collectively form the hemorrhoid treatment device. The elongated upper portion, interior facing surface aligns with the curved section, interior facing surface; the curved section, interior facing surface aligns with the base portion, interior-facing surface; the upper portion, exterior facing surface aligns with the curved section, interior facing surface; and the curved section, interior facing surface aligns with the base portion, interior-facing surface. The hemorrhoid treatment device typically includes: a left-side wall having a left-side, human skin-engaging portion and a left-side, rear wall engaging portion on the opposite side of the left-side wall of the left-side, human skin-engaging portion; a right-side wall having a right-side skin-engaging portion and a right-side, rear wall engaging portion opposite the right-side skin-engaging portion; and a back wall extending from the top edge to a back wall bottom portion wherein the back wall is interconnected with the left-side wall and the right-side wall. The right-side, skin-engaging portion and the left-side, skin-engaging portion define a front gap distance that is smaller than the width of the back wall; a planar handle engaged with the back wall and having a handle top edge in the same or substantially in the same plane as a plane defined by the top edge of the elongated upper portion of the hemorrhoid treatment device; and a spout on an end of the base portion distal the curved portion.

The method further optionally includes the steps of: adding a hemorrhoid treatment liquid chosen from the group consisting of: water, and a combination or solution of water and sodium chloride, hydrocortisone, lidocaine, witch hazel, an essential oil, lavender oil, an analgesic, or mixtures thereof into the space between the left-side wall and the right-side wall prior to use; optionally frictionally fitting an extension bracket to the main hemorrhoid treatment device wherein engagement of the extension bracket into engagement with the main hemorrhoid treatment device is achieved by applying a finger force or other force of a human to either or both of the hemorrhoid treatment device and the extension bracket to temporarily flex them and, once the lateral extension rim of the extension bracket is in an aligned position with the groove of the main hemorrhoid treatment device, releasing them to allow the snap-fit engagement; and optionally frictionally fitting a second extension or more extension brackets to the extension bracket wherein engagement is achieved by applying a finger force or other force of a human to either or both of the first extension attachment or the second or more extension brackets to temporarily flex them, and one the lateral extension rim of the extension attachment aligns with the groove of the second or more extension brackets or the lateral extension rim of the second or more extension brackets aligns with the groove of the extension attachment, releasing them to allow the snap-fit engagement. The method also typically includes the steps of positioning the hemorrhoid treatment device between a user's buttocks and/or on the perineum and holding the hemorrhoid treatment device in position without the use of a user's hands; delivering water from the shower or other water source to enter the hemorrhoid treatment liquid receiving opening of the hemorrhoid treatment device or a hemorrhoid treatment liquid receiving opening of an extension bracket; allowing gravity to cause the water or a combination or solution of water and a component chosen from the group consisting of: sodium chloride, hydrocortisone, lidocaine, witch hazel, an essential oil, lavender oil, an analgesic, or mixtures thereof wash over the user's hemorrhoid or hemorrhoids for a period of time sufficient to pass through the interior of the hemorrhoid treatment device and over or otherwise into contact with and thereby treat the user's hemorrhoid or hemorrhoids while the user is standing in a position where water is provided from the shower or other water source; and dispensing the water or the combination or solution of water and the component from the hemorrhoid treatment device or the combined hemorrhoid treatment device and extension bracket system through the spout.

These and other aspects, objects, and features of the present disclosure and claimed invention will be understood and appreciated by those skilled in the art upon studying the following specification, claims, and appended drawings.

DETAILED DESCRIPTION OF EMBODIMENTS

Figure 2:
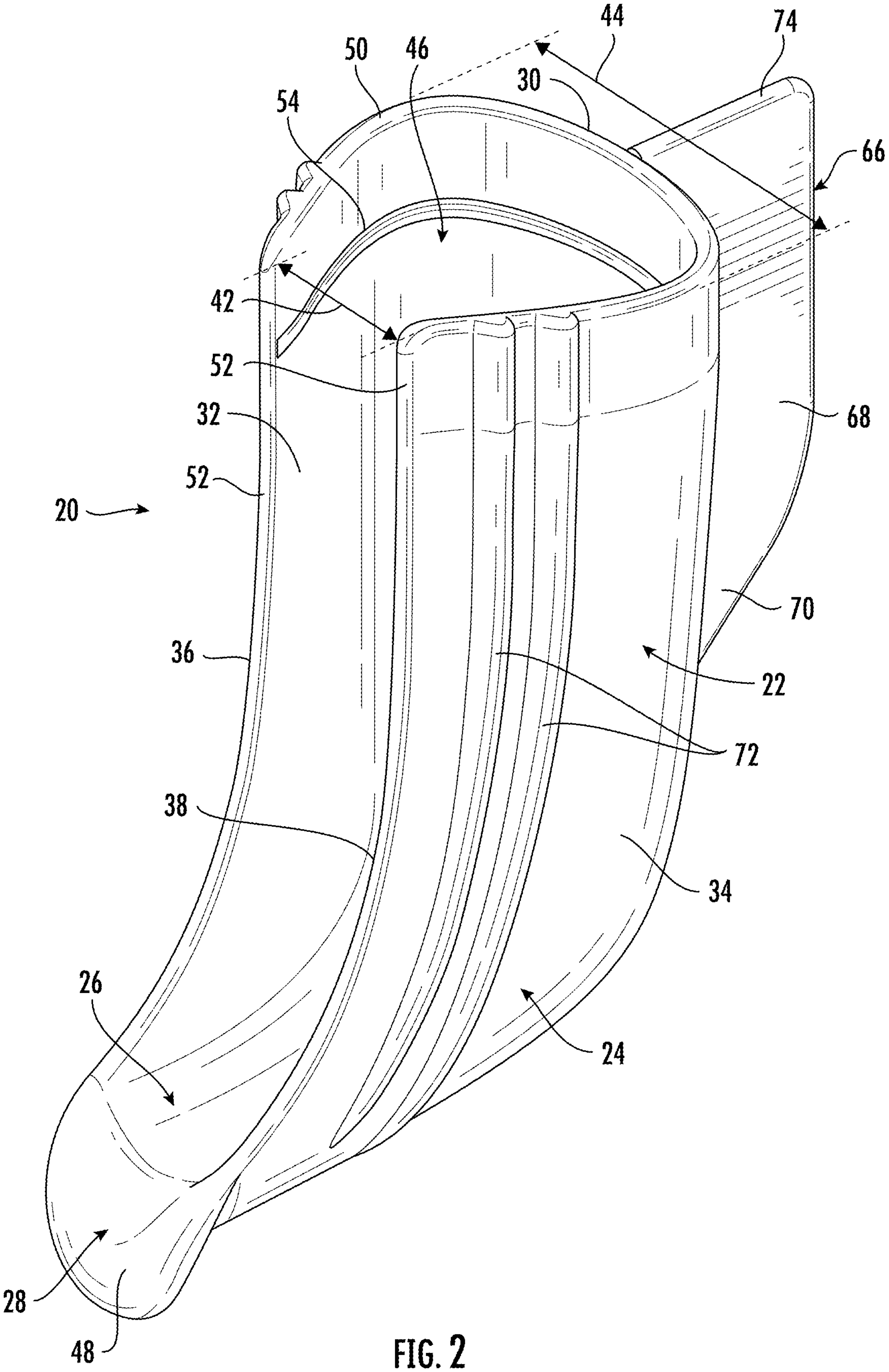
FIG. 2 is a front upper right perspective view of a hemorrhoid treatment device of the present disclosure.
Figure 3:
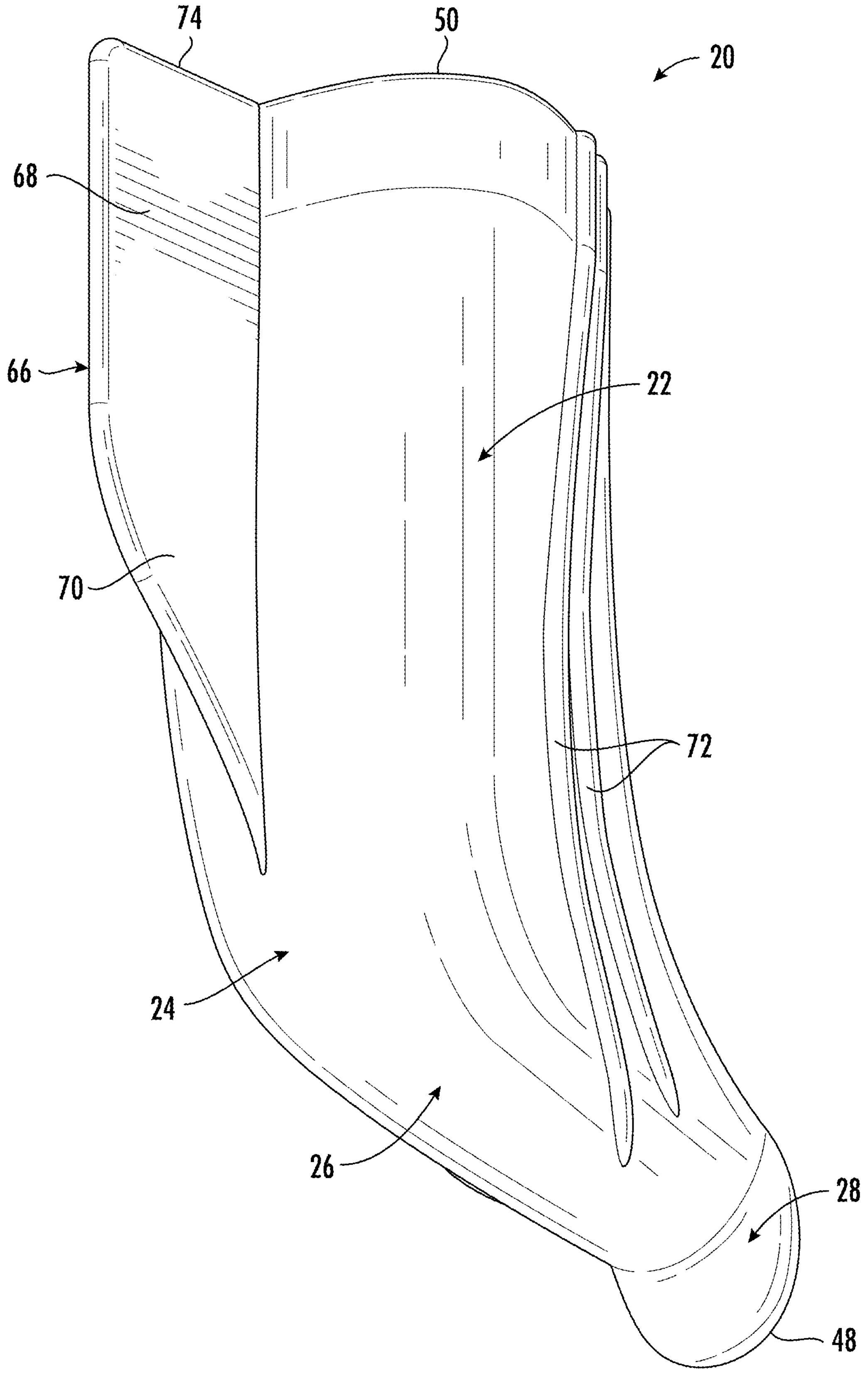
FIG. 3 is a rear bottom left perspective view of a hemorrhoid treatment device of the present disclosure.
Figure 4:
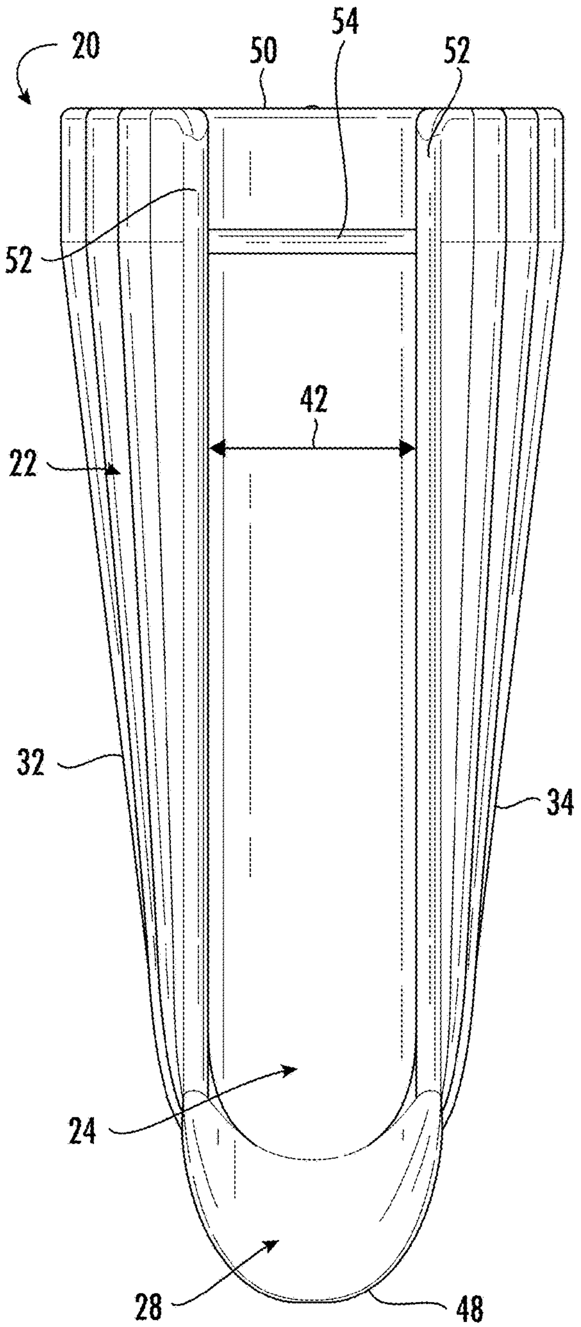
FIG. 4 is an elevated front view of a hemorrhoid treatment device of the present disclosure.
Figure 5:
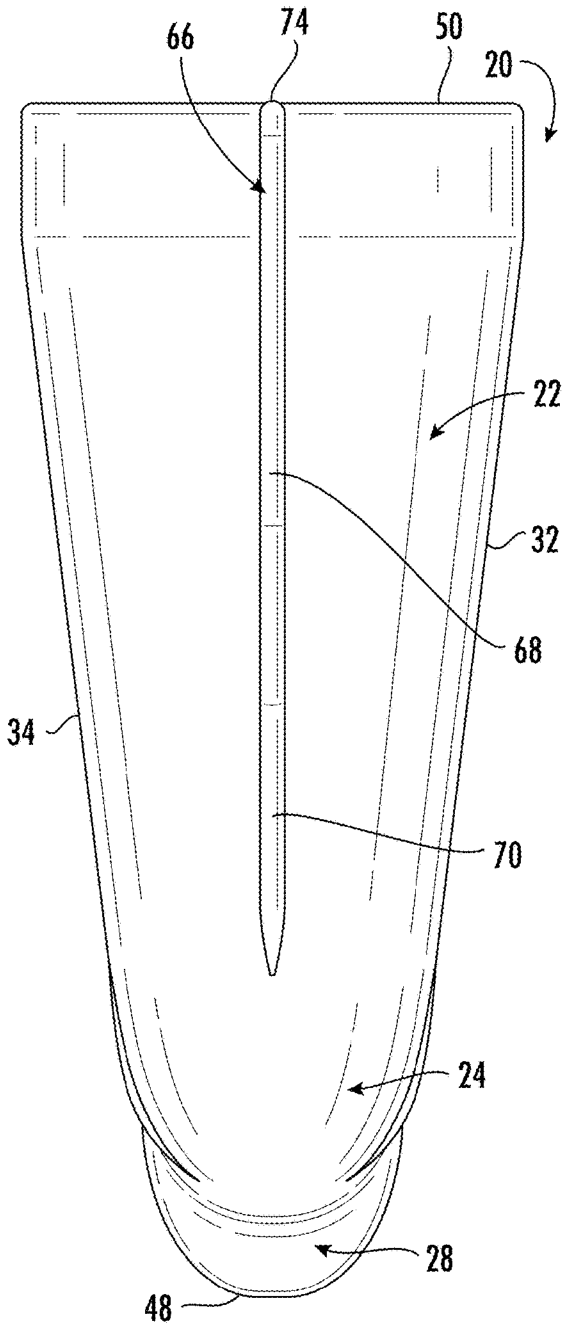
FIG. 5 is an elevated back view of a hemorrhoid treatment device of the present disclosure.
Figure 6:
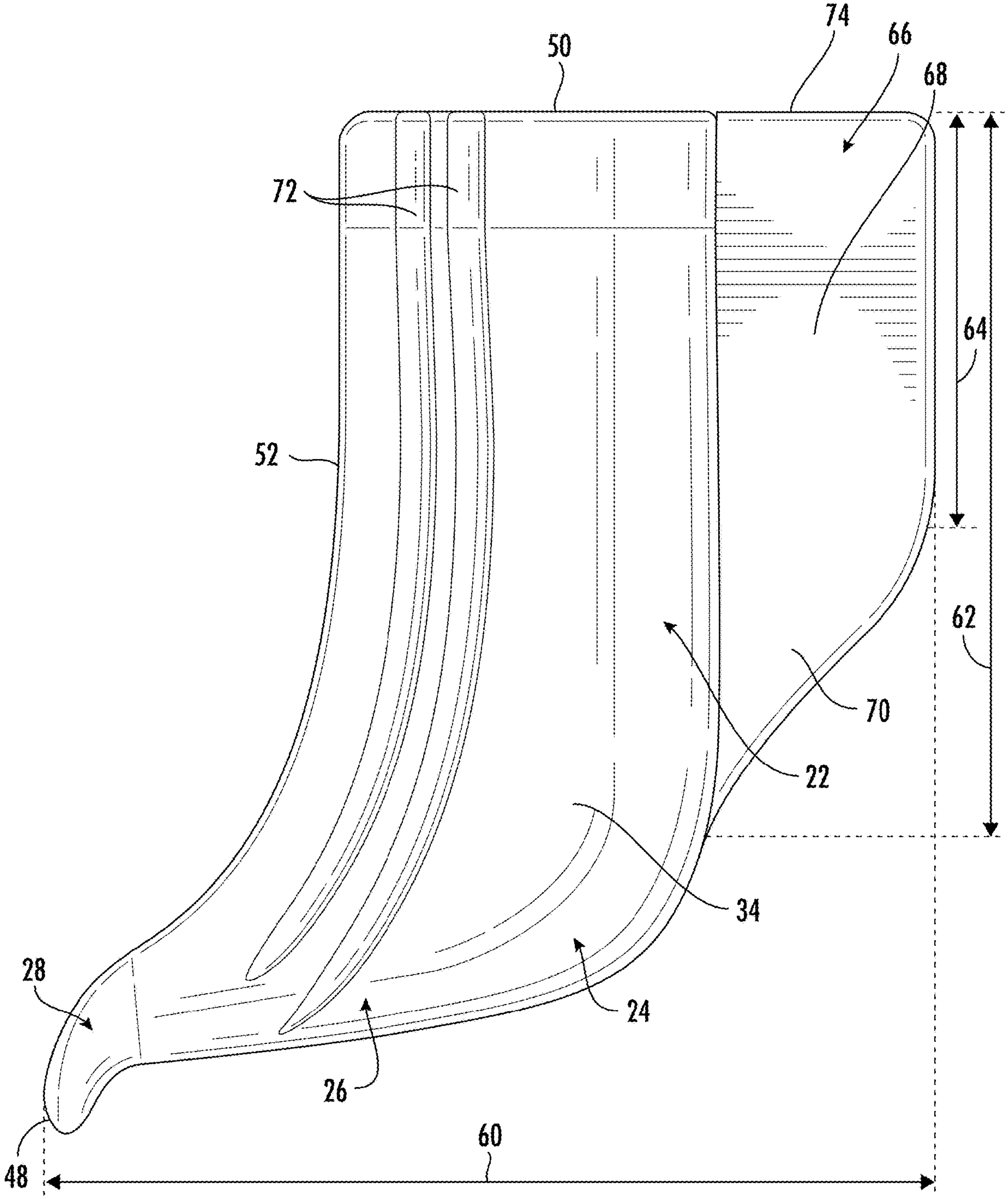
FIG. 6 is a right-side view of a hemorrhoid treatment device of the present disclosure.
Figure 7:
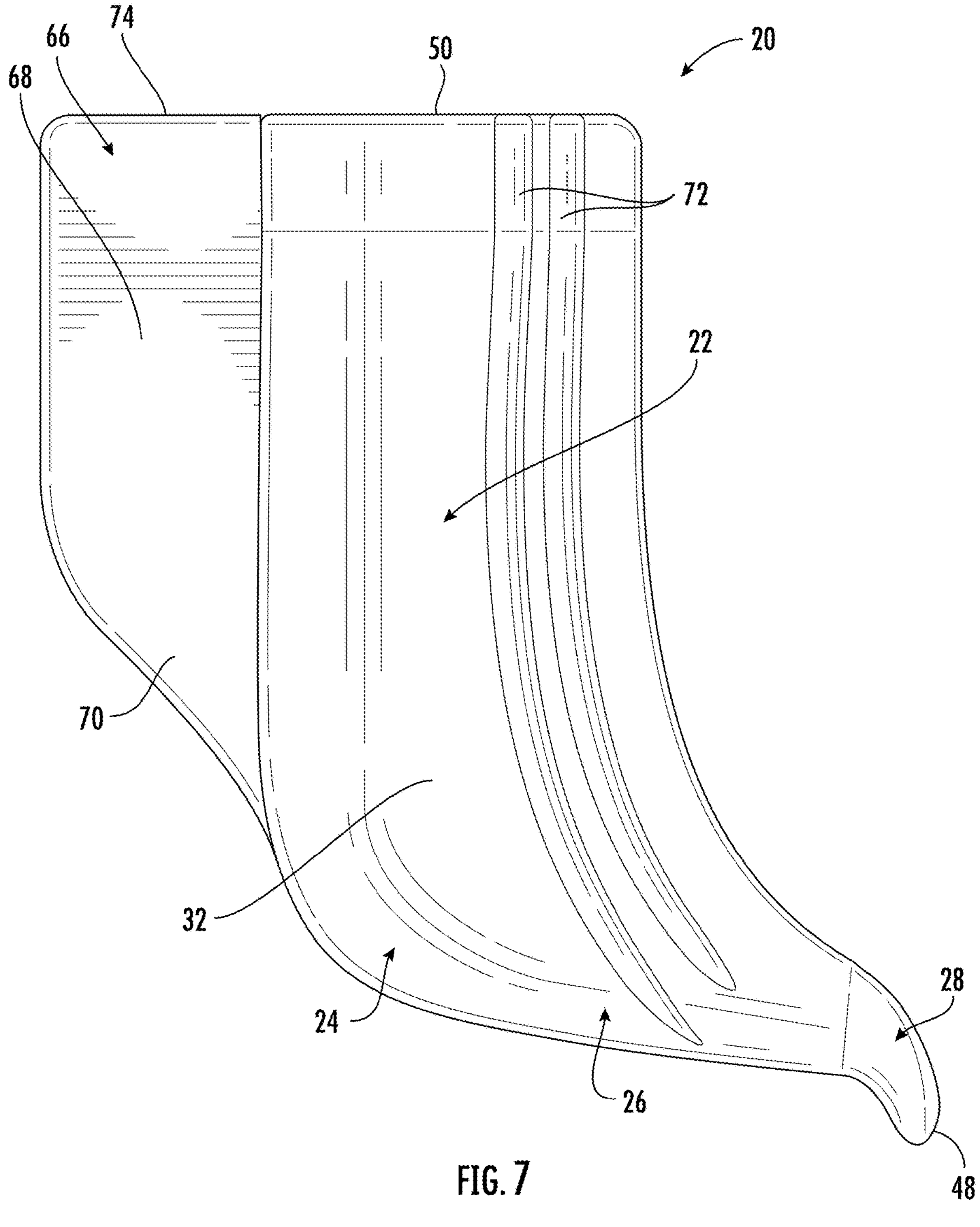
FIG. 7 is a left-side view of a hemorrhoid treatment device of the present disclosure.
Figure 8:
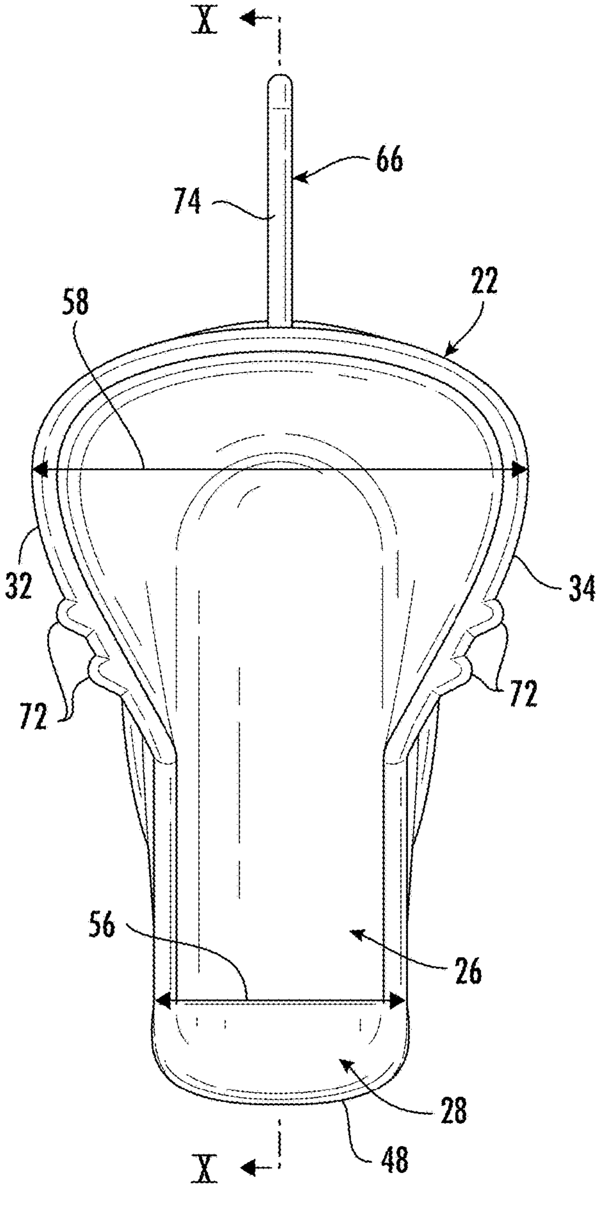
FIG. 8 is a top view of a hemorrhoid treatment device of the present disclosure.
Figure 9:
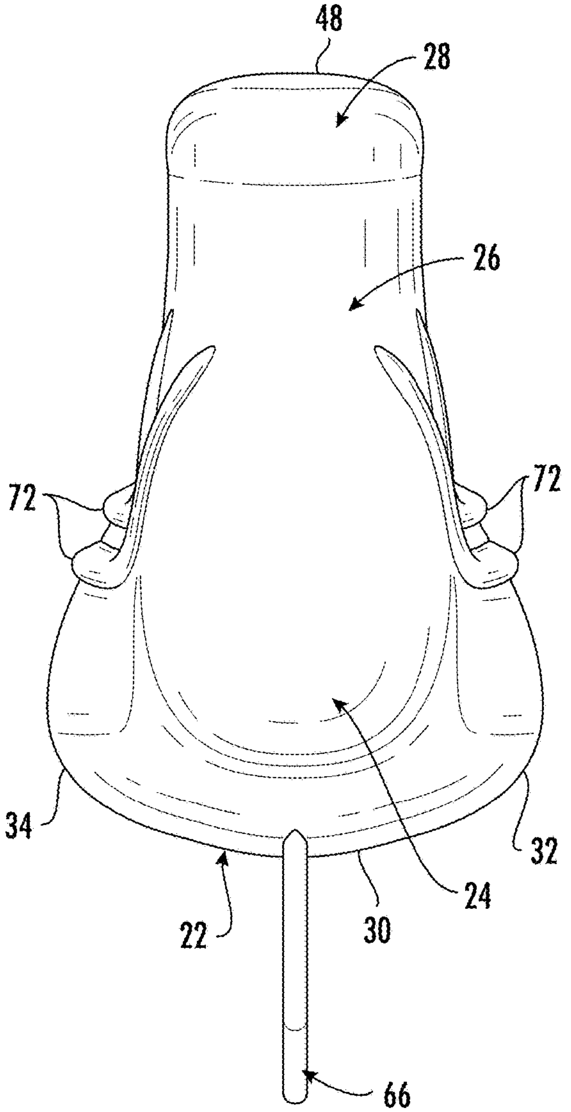
FIG. 9 is a bottom view of a hemorrhoid treatment device of the present disclosure.
Figure 10:
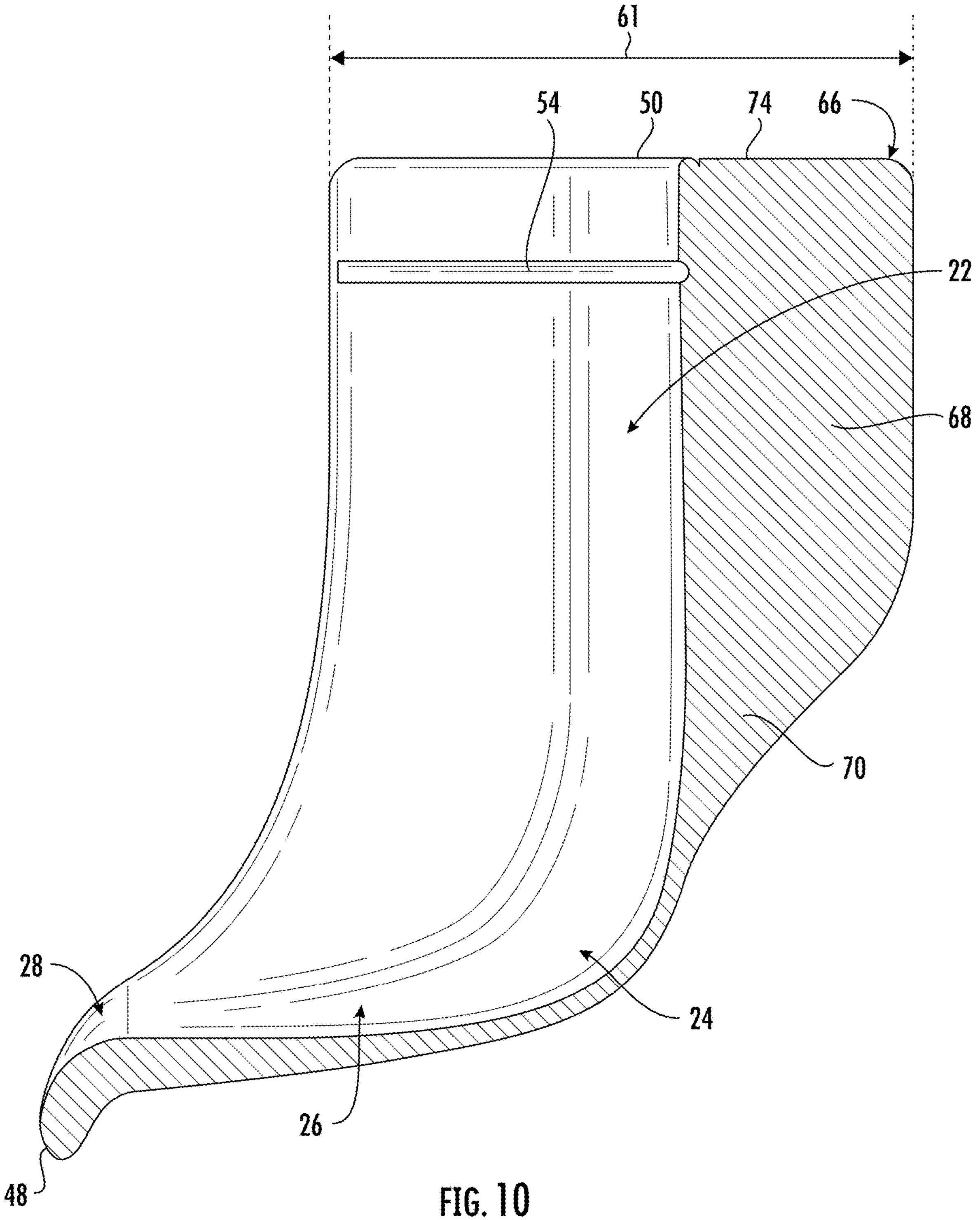
FIG. 10 is a cross-section view of a hemorrhoid treatment device of the present disclosure taken along line X-X in FIG. 8.

For purposes of description herein, the terms "upper," "lower," "right," "left," "rear," "front," "vertical," "horizontal," and derivatives thereof shall relate to the invention as oriented in FIG. 2. However, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

It will be understood by one having ordinary skill in the art that construction of the described invention and other components is not limited to any specific material. Other exemplary embodiments of the invention disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure and claimed invention, and further it is to be understood that such concepts are intended to be covered by the following claims unless these claims by their language expressly state otherwise.

It is to be understood that the disclosed innovations may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the scope of the present disclosure. The upper and lower limits of these smaller ranges may independently be included in the smaller ranges, and are also encompassed within the scope of the present disclosure, subject to any specifically excluded limit in the stated range. Where the stated range includes one or both of the limits, ranges excluding either or both of those included limits are also included in the scope of the present disclosure. All ranges and parameters, including but not limited to percentages, parts, and ratios, disclosed herein are understood to encompass any and all sub-ranges assumed and subsumed therein, and every number between the endpoints. For example, a stated range of "1 to 10" should be considered to include any and all sub-ranges beginning with a minimum value of 1 or more and ending with a maximum value of 10 or less (e.g., 1 to 6.1, or 2.3 to 9.4), and to each integer (1, 2, 3, 4, 5, 6, 7, 8, 9, 10) contained within the range. In this specification and the appended claims, the singular forms "a," "an" and "the" include plural reference unless the context clearly dictates otherwise. All combinations of method steps or process steps as used herein can be performed in any order, unless otherwise specified or clearly implied to the contrary by the context in which the referenced combination is made.

To the extent that the terms "includes" or "including" or "have" or "having" are used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A" or "B" or both "A" and "B". When the Applicant intends to indicate "only A or B but not both" then the term "only A or B but not both" or similar structure will be employed. Thus, use of the term "or" herein is the inclusive, and not the exclusive use. Also, to the extent that the terms "in" or "into" are used in the specification or the claims, it is intended to additionally mean "on" or "onto." In this specification and the appended claims, the singular forms "a," "an" and "the" include plural reference unless the context clearly dictates otherwise.

Figure 1:
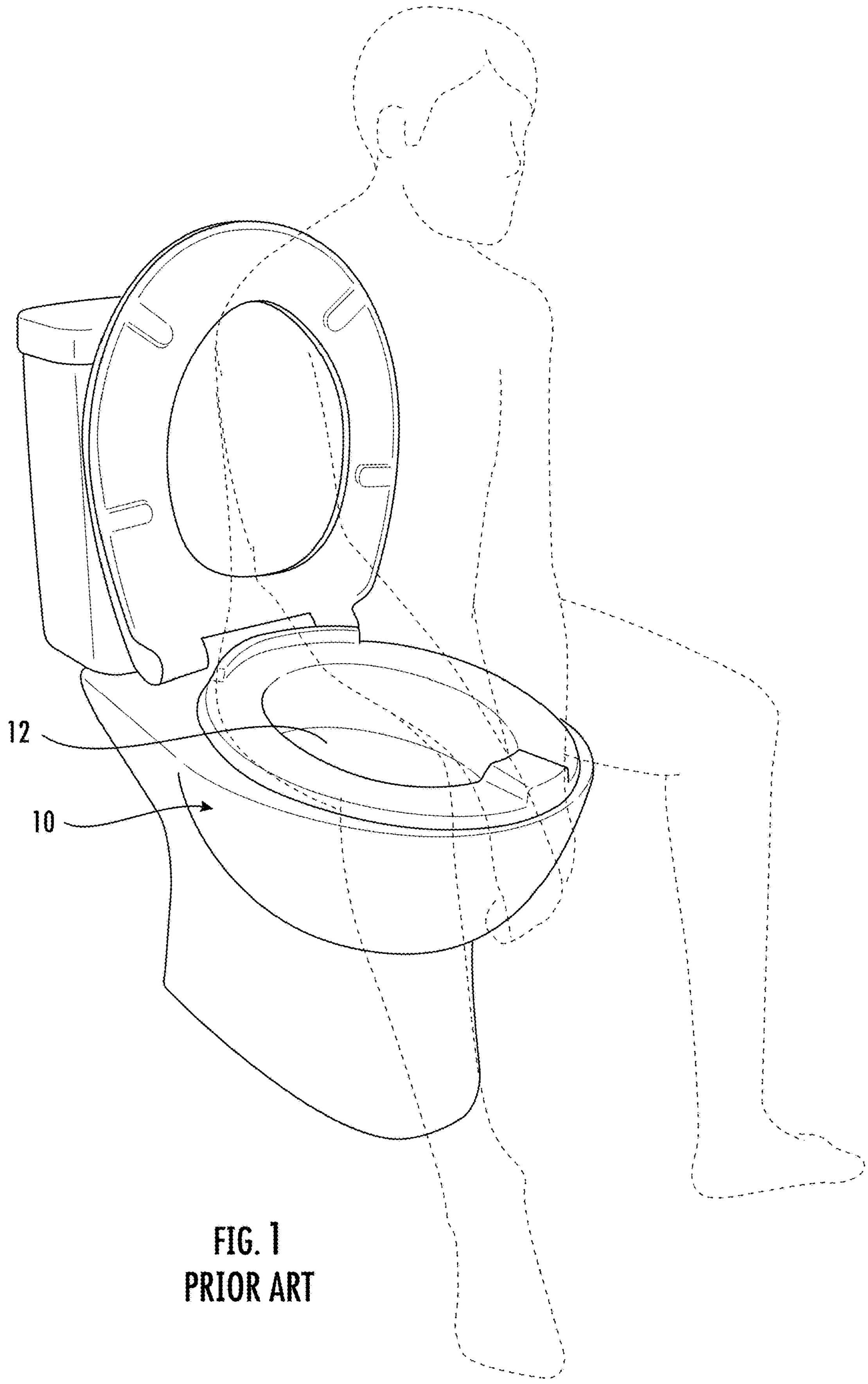
FIG. 1 PRIOR ART
FIG. 1 is an example of a prior art toilet where one might dip the anus region containing the hemorrhoid(s) into the water of the toilet or other bowl and attempt to hold the region in contact with the water and optional treatment composition dissolved in the water.

Displayed in FIG. 1 is a representation of the prior art, wherein a person afflicted with hemorrhoids would immerse their anal region into medicine saturated water sitting in an open container such as a toilet.

FIGS. 2-10 generally show a main anorectal device that may be used to treat hemorrhoids and/or anal fissures or an injury after anorectal procedures. The devices of the present disclosure may also be used to treat or for therapy for anal fistula after surgery. The anorectal device is typically used as a hemorrhoid treatment device 20 with optionally one or a plurality of extension attachments 40. The main hemorrhoid treatment device 20 typically includes an elongated upper portion 22, a curved midsection 24 and a laterally extending base portion 26. The elongated upper portion 22, curved midsection 24 and laterally extending base portion 26 are typically formed into a continuous main hemorrhoid treatment device 20 so that all portions are smooth and without sharp edges and so that there is little or no chance of water leakage from an interior of the main hemorrhoid treatment device 20 to the exterior of the main hemorrhoid treatment device 20. However, conceivably, the sections could be joined together from one or more components so long as a water tight seal or an at least substantially water tight seal is maintained during use between each of the elongated upper portion 22, curved midsection 24 and laterally extending base portion 26. The overall main hemorrhoid treatment device 20 is generally L-shaped with a left-side wall 32, a right-side wall 34, and a back wall 30 there between. The side walls couple to the back wall 30 on their distal sides and have a front facing, left skin engaging edge 36 and a front facing, right skin engaging edge 38. The front facing, left skin engaging edge 36 and the front facing, right skin engaging edge 38 that approach one another typically do not touch without an outside force being applied thereto and are shape retaining unless an outside force is applied to them and/or the left-side wall and/or the right-side wall. Typically, the overall main hemorrhoid treatment device 20 is typically constructed of metal or plastic that is smooth, but could conceivably be constructed of a fairly rigid silicon material or other material as well. Optionally, the metal may be a surgical grade metal such that it may be sterilized when the device is used in a medical environment such as a hospital or clinic, but more often, the overall device is made of a plastic material that can be washed readily in a user's home sink or potentially a dishwasher to ensure sanitary use each time. The plastic or metal material is also less likely to cause irritation or abrasion during use in the shower. The front facing, left skin engaging edge 36 and the front facing, right skin engaging edge 38 each typically have a slightly outwardly extending brim 52 that extends outwardly away from the interior of the main hemorrhoid treatment device 20 thereby creating a smooth surface for the skin to contact and provide a more comfortable engagement with the user's sensitive perineum, anus and buttocks areas.

Figure 12:
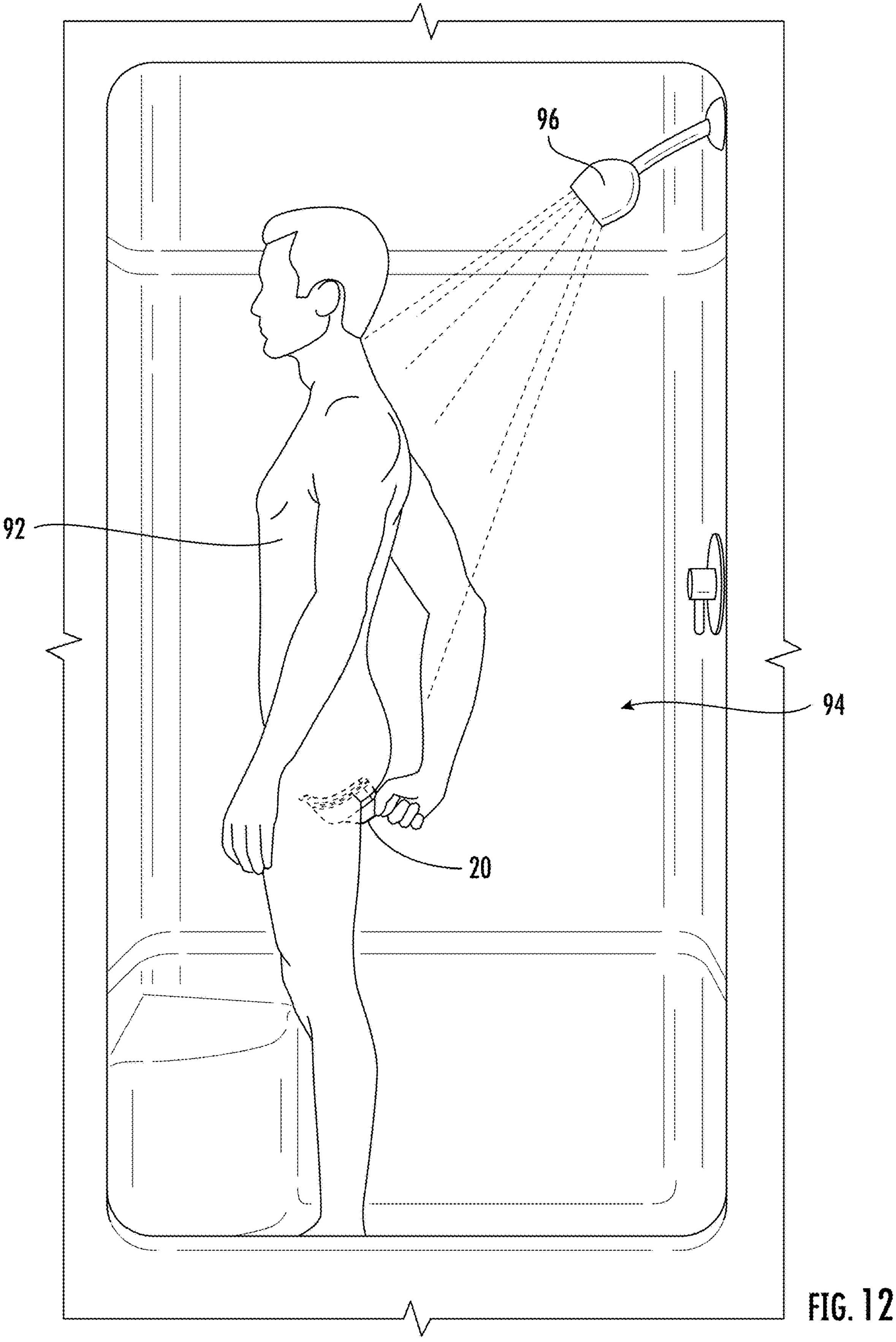
FIG. 12 is an isometric view of a person engaging a hemorrhoid treatment device of the present disclosure into a treating position between the buttocks and covering the perineum and the anal areas.
Figure 13:
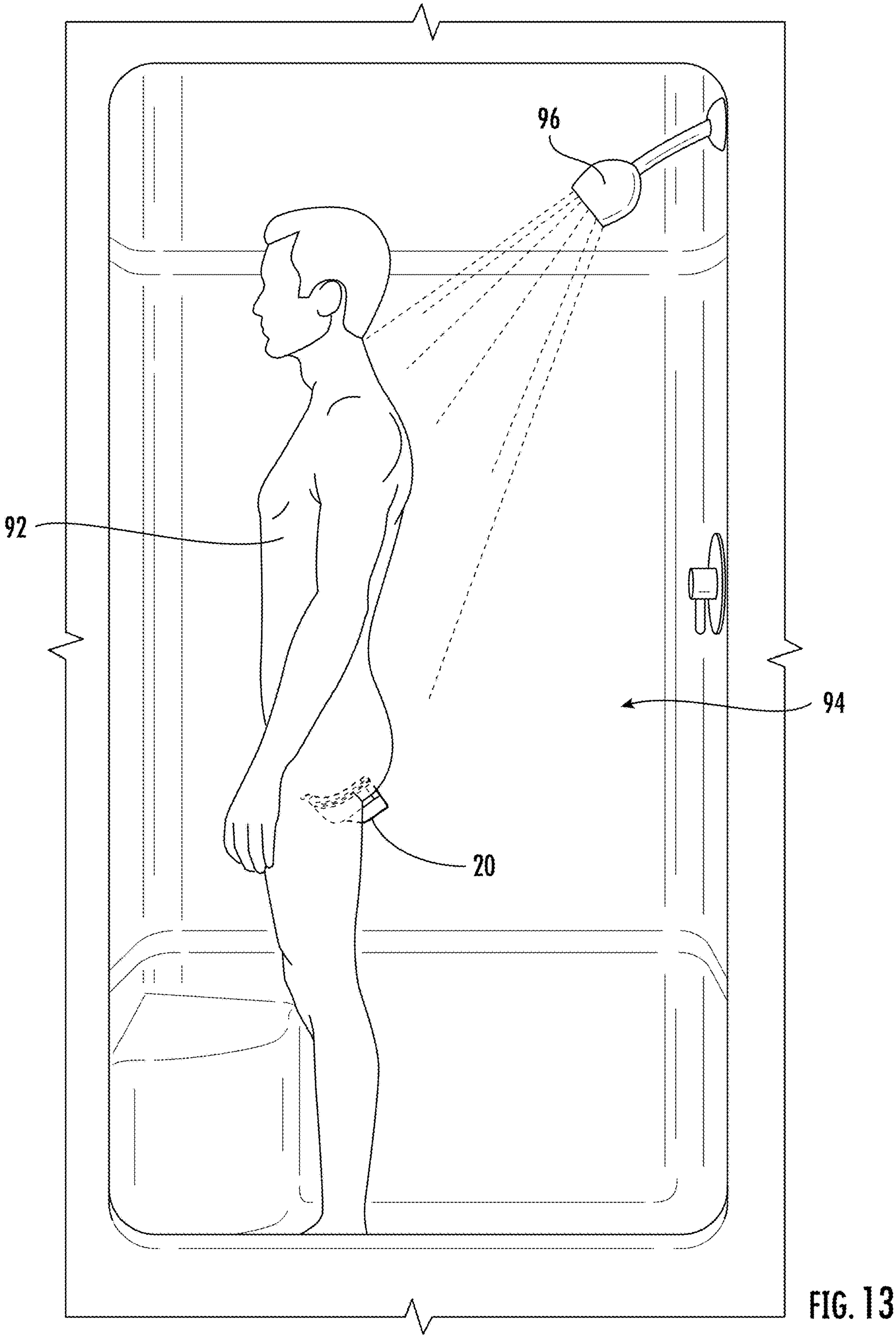
FIG. 13 is an isometric view of a person standing within the shower with a hemorrhoid treatment device of the present disclosure held in position in a normal standing position without any permanent engagement with the person or strapping of the device in position.
Figure 14:
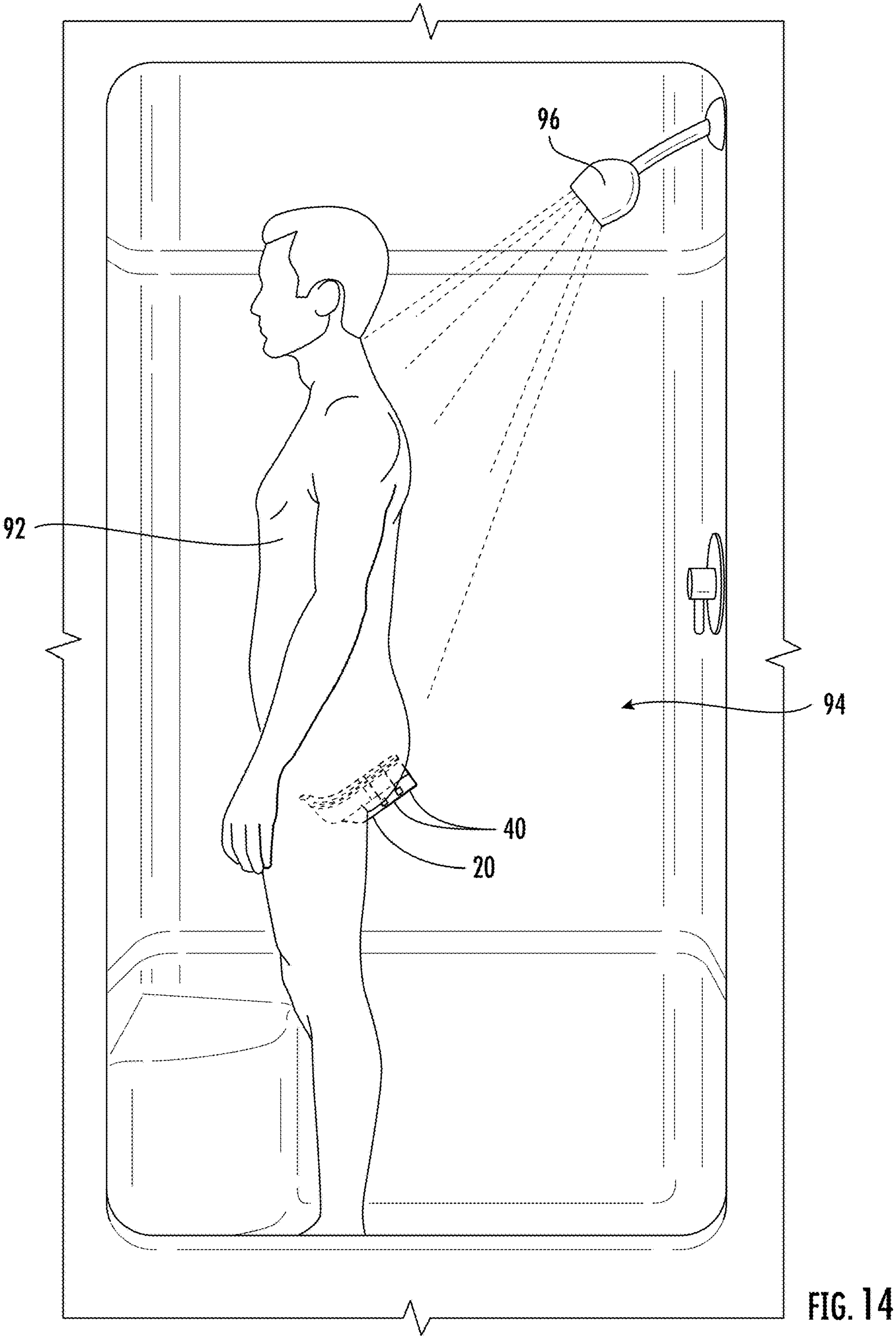
FIG. 14 is an isometric view of a person standing within the shower with a hemorrhoid treatment device of the present disclosure held in position in a normal standing position without any permanent engagement with the person or strapping of the device in position where the person is a taller or bigger/heavier person with the need for one or two or more extension attachments engaged to the main hemorrhoid treatment device of the present disclosure to allow the device to more readily capture water from the shower and apply the water and optional medicinal composition(s) to the hemorrhoid containing area(s) of the person.

The front gap distance 42 between the front facing, left skin engaging edge 36 the front facing, right skin engaging edge 38 is typically less than the width 44 of the back wall, the back portion being most typically twice as wide as the distance between front facing, left skin engaging edge 36 and the front facing, right skin engaging edge 38. The skin engaging edges of the side walls are parallel with one another. The side walls are both typically molded as to fit in between the user's buttocks and the laterally extending portion substantially along the perineum of the user such that the overall main hemorrhoid treatment device 20 is retained in place when the user is standing while still allowing the opening 46 to receive warm water from the shower or other warm water delivery method. Optionally, the main hemorrhoid treatment device 20 may engage with a belt or strap that wraps around the user's midsection to help retain the device in position as well. The warm water source is typically a shower as shown in FIGS. 12-14, but can be any other source of warm water, but is typically a relatively constant source of warm flowing water delivered from a position above the main hemorrhoid treatment device 20 when in use.

The curved midsection 24 and laterally extending base portion 26 provide the main hemorrhoid treatment device 20 with the overall general L-shape, typically designed to roughly match the average human anatomy of the area around the perineum past the anus and up the buttocks. The overall configuration of the main hemorrhoid treatment device 20 arrangement of the walls creates a trough passageway within the interior of the walls that channels water received through the opening 46 that then travels through using the force of gravity through the trough and out the lip end section 28. The lip end section has a downward pour spout 48 exit location that allows the warm water from the water source to travel out the bottom of the trough. The trough begins at the opening of the top edge 50, which typically has a general horseshoe-shaped cross section; however, the trough may be consistently or substantially consistently the same distance from the left-side wall to the right-side wall or the trough may instead gradually narrow along the elongated upper portion, the curved midsection and laterally extending base portion until the trough interior terminates at the spout 48 of the lip end section 28.

A groove or channel 54 may be located within the trough near the top edge and is typically configured as to allow an extension attachment or attachments 40 to interface with the main hemorrhoid treatment device 20 and extend the device's trough length to accommodate larger human users more easily as discussed herein. Optionally, a plurality of horizontally extending grooves may be used. The groove or grooves, when employed, are typically constructed such that the groove or grooves project into the interior of the main hemorrhoid treatment device 20 or provide a channel on the interior facing surface of the main hemorrhoid treatment device 20 proximate the top of the device and are sized to allow for a snap-fitting male and female engagement between an extension attachment 40 and the main hemorrhoid treatment device 20. The engagement is typically friction fit and engagement is achieved by applying a finger force of a human to either or both of the main hemorrhoid treatment device 20 and the extension attachment 40 to temporarily flex them and, once in aligned position, releasing them to allow the snap-fit engagement. Sometimes, the components may need to be slid into a friction fit upon release of the force, but this is not necessarily the case. The groove 54 is typically horizontally oriented and typically stretches across the entire top portion of the elongated upper portion of the main hemorrhoid treatment device 20.

The main hemorrhoid treatment device 20 typically has a length of from about two inches to about three inches, more typically about 2¼ inches from the spout to the back wall 30. The main hemorrhoid treatment device 20 typically has an overall depth 60 of from about two inches to about four inches, more typically about three inches from the front edge of the spout 48 to the back edge of the handle 66. The widest portion 58 of the elongated upper portion 22 of the main hemorrhoid treatment device 20 typically is about two inches. The width 56 of the lip end section 28 is typically from about ½ inch to one inch, more typically about ¾ inch in width. The depth 61 of the main hemorrhoid treatment device 20 from the front facing, left skin engaging edge 36 and the front facing, right skin engaging edge 38 to the back wall is typically about 1 5/16 inches.

A pair of ridges 72 that substantially mirror one another in shape and general dimension are typically integrally formed in the left-side wall and the right-side wall of the main hemorrhoid treatment device 20. The ridges 72 are positioned generally parallel to one another, and typically start at the top edge 50 and typically run continuously along the side walls before gradually tapering away along the laterally extending base portion 26. Both pairs are closer to the skin engaging sides of the associated walls then to the side walls' distal ends proximate the back wall. The ridges provide a secure hold for the device 20 inside the user's buttocks by increasing friction to grip to human skin. They also provide durable structural support for the device during use and storage to provide strength to the overall device.

A handle 66 is engaged with and typically integral with the back wall 30. While conceivably the handle might be removable, the integral nature of the handle helps facilitate its use behind the person when the person is self-installing the device in position for treatment. It is impossible to have the handle inadvertently disengage from the rest of the device when it is integrally formed with the rest of the device. The integral nature of the handle with the device is preferred. The handle 66 typically has a handle main portion 68 that has a greater depth and is the primary area a user would grip the device while it is being positioned for use and when it is being removed. The handle 66 will also typically have a tapered handle curved portion that tapers down to create a smooth surface that terminates proximate the bottom of the back wall and the curved midsection. The handle is ideally positioned to easily allow the user to manipulate the main hemorrhoid treatment device 20 when the user's hemorrhoids are undergoing treatment. The handle has a top edge 74 having a surface that is in the same plane or substantially the same plane as the plane defined by the top edge 50 of the elongated upper portion. The handle main portion 68 has a height 64 along the back wall of typically from about one to two inches, more typically about 1½ inches. The overall height of the handle 62 from the top edge to where the handle's opposite end meets with the back portion is typically a length of from about 1 inch to about 3 inches, more typically from about 1½ inches to about 2½ inches, and most typically about 2¼ inches.

Figure 11:
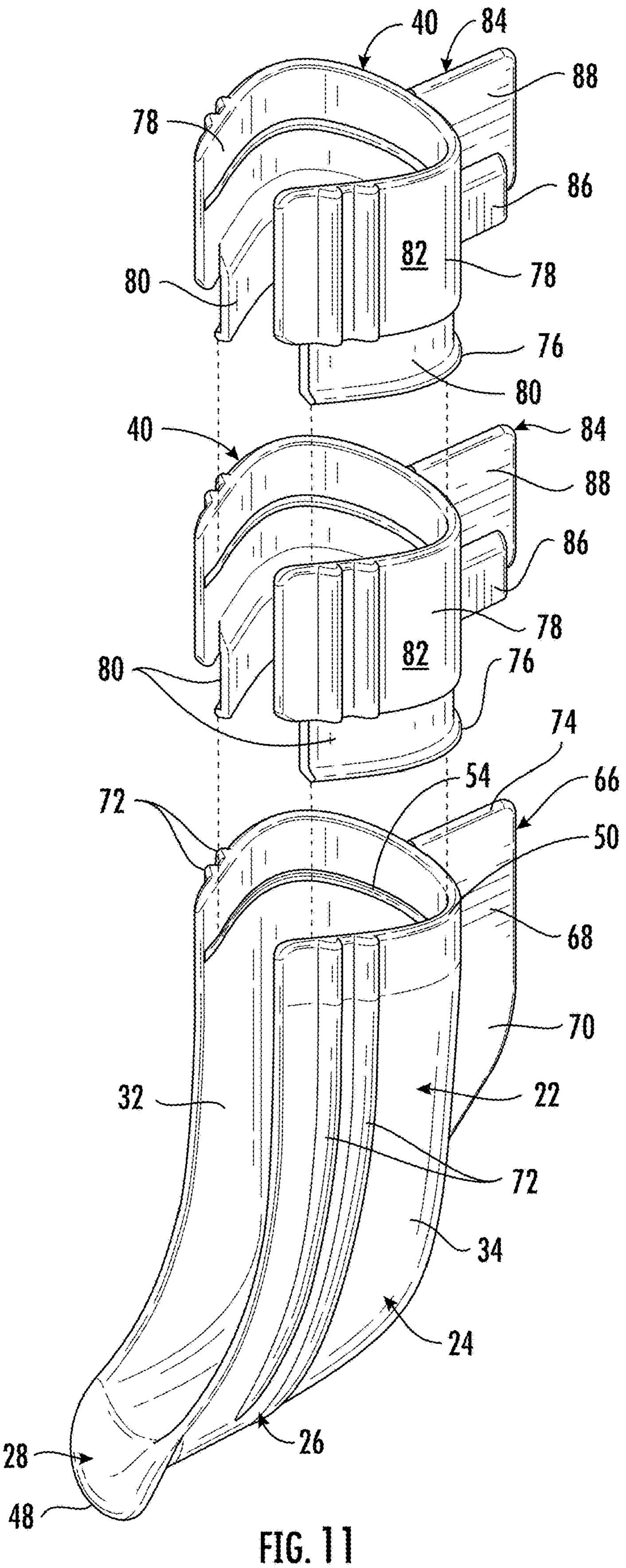
FIG. 11 is an exploded view of a hemorrhoid treatment device of the present disclosure showing two optional snap-fit extension attachments mounting to the top of the hemorrhoid treatment device in a snap-fit engagement of the present disclosure thereby extending the length thereof in order to allow for the device to be used with humans that are taller or bigger.

As shown in FIG. 11, the present disclosure includes the main hemorrhoid treatment device 20 that may be optionally connected with one or a plurality of extension attachments 40. The one or, as shown in FIG. 11, two or more extension attachments 40 couple with one another and are frictionally held in engagement with one another within the groove 54 by mating the lateral extension rim 76, but is the male of the male and female connection with the groove 54 of the main hemorrhoid treatment device 20. Each of the extension attachments 40 typically have main body 78, an interior surface engaging, downwardly extending projection 80. When engaged with the main hemorrhoid treatment device 20 the extension attachment(s) 40 are designed to appear to the naked human eye to be integral with the main hemorrhoid treatment device 20. The outer surface 82 of the extension attachments 40, when in the unbiased and natural state have the same corresponding cross-sectional shape as the main hemorrhoid treatment device's elongated upper portion that the extension attachment 40 is designed to mate with to extend the length of the device. As discussed herein, the interior surface engaging downwardly extending projection 80 engages the interior surface top of the elongated upper portion or another extension attachment. The interior surface engaging downwardly extending projection 80 typically has a smaller cross-sectional area, typically 1⅛ inches from front to back, than the main body 78 of the extension attachment 40. The interior surface engaging downwardly extending projection 80 typically extends below the outer portion by about 7/16 inches. The main body portion 78 of the typical extension attachment 40 has a height of about one inch. The extension attachment 40 also typically includes an extension attachment fin 84 that operates to essentially align with and extend the handle 66 of the main hemorrhoid treatment device 20. The fin 84 typically has a main portion 88 of the fin that is a substantially planar portion and a downwardly facing U-shaped retainer 86 that extends below the bottom surface of the fin 84 such that two sides of the downwardly facing U-shaped retainer 86 form a channel that has a diameter from one side to the other of approximately the same distance as the thickness of the handle 66 such that when the extension attachment is installed on either the main hemorrhoid treatment device 20 or another extension attachment 40 the downwardly facing U-shaped retainer 86 friction fits over a top segment of the handle and prevents rotation of the extension attachment and more securely holds it in position during use. The outer surface 82 of the extension attachment 40 typically has a pair of ridges 90 on the left and right side that are designed and positioned to align with the ridges 72 of the main hemorrhoid treatment device 20. These two ridges on each side of the device, similar to those on the main hemorrhoid treatment device 20 provide structural support, but also finger actuating grooves that facilitate an inward finger force being applied to move the left-side wall and right-side walls closer together so that the extension attachment can more readily be positioned to friction fit engage the main hemorrhoid treatment device 20 or another extension attachment. The ridges facilitate squeezing the walls together. The ridges 90 of the extension attachment typically substantially align with both the ridges 72 and ridges of any additional extension attachments 40 that may be used when all are in the engaged position for use of the device.

The extension attachments can be removably engaged with one another or a main hemorrhoid treatment device 20 by hand and without the use of tools. A plurality of extension attachments can be coupled to one another and to the main hemorrhoid treatment device 20, enabling the user to customize its size to be an appropriate size for their treatment and allow the device to be used by multiple users with different body types and anatomy lengths, for example.

As shown in FIG. 12 the main hemorrhoid treatment device 20 may be used by the user 92 grabbing the handle 66 of the main hemorrhoid treatment device 20 and placing it in position underneath the perineum and the anus region and between the buttocks such that opening 46 is at least partially upward facing when the user 92 is standing. The upward facing direction of the opening is designed to receive water, typically warm or hot water at a temperature of from about 80° F. to about 115° F., thereby allowing the water to gently flow past the one or more hemorrhoids to be treated and out the bottom of the main hemorrhoid treatment device 20. The main hemorrhoid treatment device 20 is typically held in place by the user's own anatomy alone without the use of any other mechanical assisting, force applying device to aid against the force of gravity. Once in position, the main hemorrhoid treatment device 20 remains in position during use unless acted upon by the user.

The user 92 may simply treat the hemorrhoid(s) with water, but may instead optionally place one or more treatment compositions into the trough of the main hemorrhoid treatment device 20 prior to installing it into the anatomy engaged position such that the composition disperses in the aqueous environment and treats the hemorrhoid(s) of the user. The delivery form of the treatment composition may include a water dissolvable tablet, a water dissolvable capsule, an effervescent tablet or a plurality of dissolvable granules of treatment composition. Salt (sodium chloride), hydrocortisone, lidocaine, and witch hazel, natural essential oils such as lavender oil (any oil discussed from a plant of the genus *Lavandula*) or another distilled essential oil such as peppermint, tea tree oil, patchouli, and eucalyptus, or any other numbing agent, analgesic or a pain reliever such as acetaminophen, aspirin or an NSAID such as Ibuprofen may be used alone or in combination as the treatment composition of the present disclosure.

FIG. 13 shows the proper usage of the device in a shower 94 with the user 92 standing such that the elevated water source, typically a shower head, positioned at a height greater than the opening 46 of the main hemorrhoid treatment device 20 delivers water (with or without a medicament) into contact with the hemorrhoid. When the user's back is facing the showerhead, water from the incoming stream is channeled into the device and activating medicine and directing it to the hemorrhoids roughly near the lip end section 28 of the device. The device allows the user to use the treatment while showering, a simple daily routine. The user will not devote as much time from their day to treat their hemorrhoids, making it very convenient to do so. The device is typically retained in position without the use of the user's hands after the hemorrhoid treatment device is installed in the use position and held in position with the force of a user's buttocks in the standing position. The device may be installed in position by hand but be hands free during use.

For a larger person, as shown in FIG. 14, the main hemorrhoid treatment device 20 may not be well exposed to the water without the use of one or more extension attachments 40 as described above. As such, the efficacy of the main hemorrhoid treatment device 20 not employing one or more extension attachments 40 is less. For this purpose, extension attachments 40, pictured during use in FIG. 14, are attached as needed until the device is long enough to take in adequate amounts of water for treatment. The extension attachments 40 typically are installed until the opening 46 of the device's last added extension attachment is oriented upward enough to capture a sufficient amount of water from the elevated water source or sources.

Figure 15:
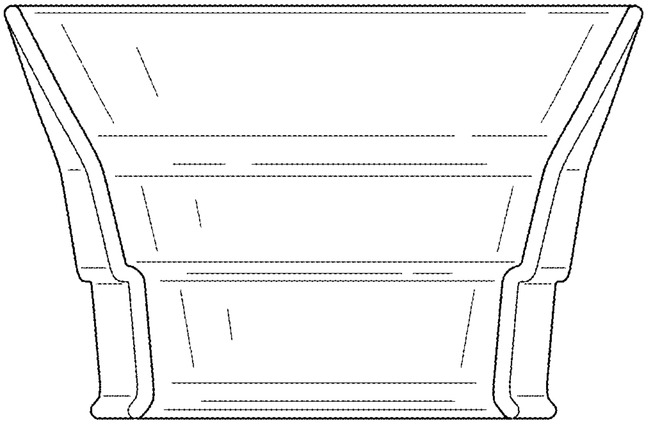
FIG. 15 is an elevated front view of a funneling attachment that may snap fit with the device of the present disclosure to capture more water flow into the top of the device.
Figure 16:
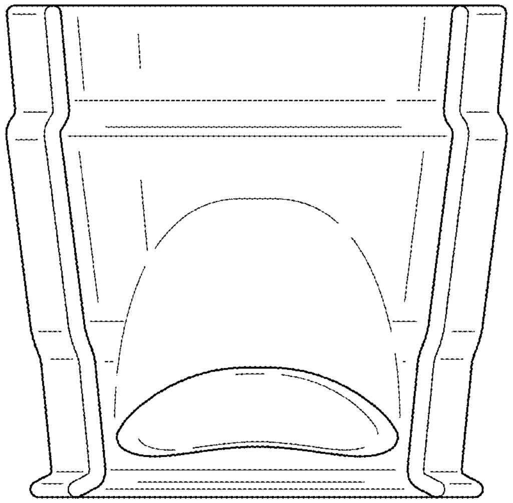
FIG. 16 is an elevated front view of an optional intermediate directional component that has a feature that directs water towards the treatment area opposite the opening on the front of the intermediate directional component.
Figure 17:
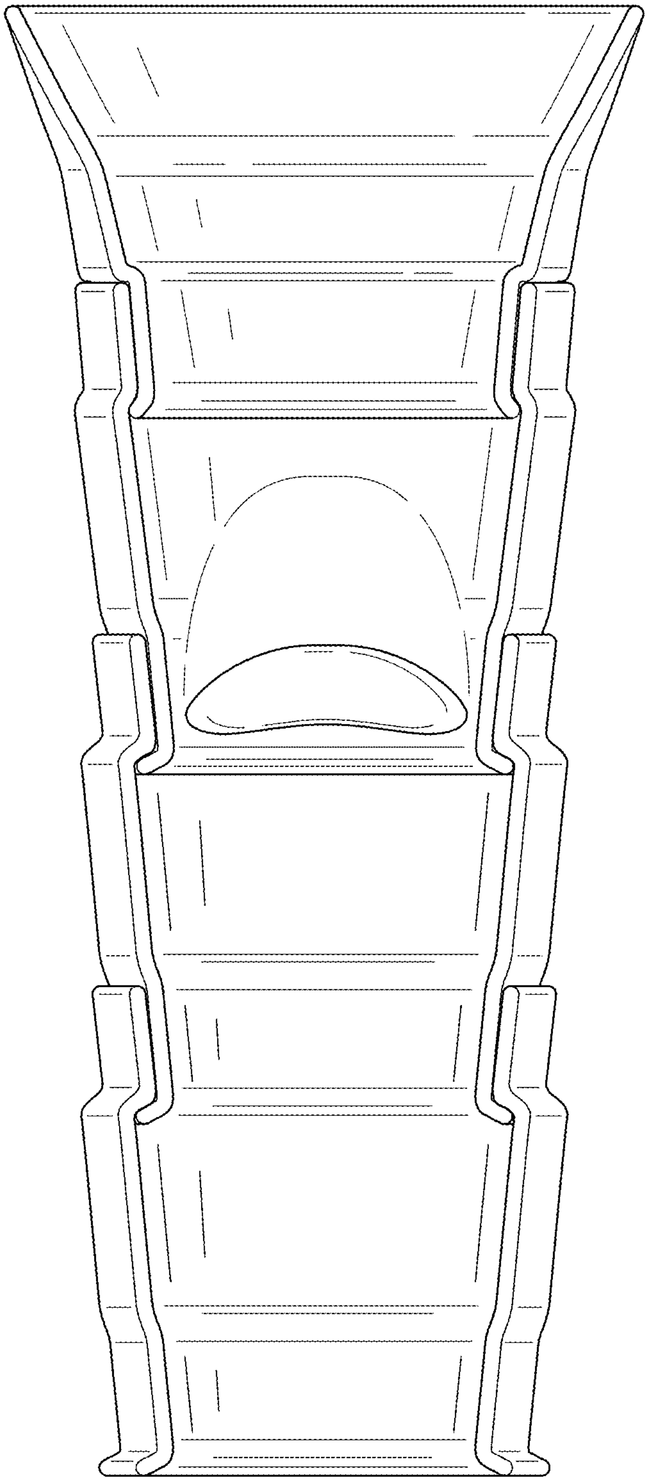
FIG. 17 is an elevated from view of the optional intermediate direction component and the funneling attachment in the snap fit engagement with an extension as shown in FIG. 11.

As shown in FIGS. 15-17, the devices of the present disclosure may utilize a variety of snap fit extensions beyond the extensions discussed above. In particular, the shower lavage devices of the present disclosure may use an intermediate component as in FIG. 16 to direct water flow more directly into contact with the area of the user to be treated by the water striking the inwardly extending shelf ledge that extends into the interior from the back of the extension. The shelf, as shown, may be curved upward to provide a slight cupped surface where the water from the shower or other elevated water source then strikes and is deflected into contact with the user's skin. FIG. 15 shows a funnel top attachment that collects the water more broadly to provide a greater amount of water to be delivered to the area of the user to be treated with the device more efficiently than if the top of the device is used, which has a smaller cross-sectional surface area. The funnel portion has a greater cross-sectional surface area than the opening at the top of the device without the funnel attachment engaged to it and the distal end of the funnel portion itself. The funnel portion is the top attachment to the device or any added extension or intermediate component, which are all designed to snap fit into engagement with one another. The funnel facilitates the filling of the device with water while the device 20 is in use. The intermediate component shown in FIG. 16 may also facilitate rotational flow of water within the device 20 while the device is in use thereby facilitating contact with the affected area being treated with the water or water and other additive as discussed above.

What is claimed is:

1. A hemorrhoid treatment device for the treatment of hemorrhoids in a human comprising:

an elongated upper portion having a top edge defining a hemorrhoid treatment liquid receiving opening, an elongated upper portion, interior facing surface, and an elongated upper portion, exterior facing surface;

a base portion having a hemorrhoid treatment liquid outlet, a base portion, interior facing surface, and a base portion, exterior facing surface;

a curved midsection spaced between the elongated upper portion and the base portion having a curved section, interior-facing surface and a curved section, exterior facing surface;

wherein the base portion, the curved midsection, and the elongated upper portion, collectively form the hemorrhoid treatment device;

wherein the elongated upper portion, interior facing surface aligns with the curved section, interior facing surface and the curved section, interior facing surface aligns with the base portion, interior-facing surface;

wherein the hemorrhoid treatment device is configured to comprise:

a left-side wall having a left-side, human skin-engaging portion and a left-side, rear wall engaging portion on the opposite side of the left-side wall of the left-side, human skin-engaging portion;

a right-side wall having a right-side skin-engaging portion and a right-side, rear wall engaging portion opposite the right-side skin-engaging portion;

a back wall extending from the top edge to a back wall bottom portion wherein the back wall is interconnected with the left-side wall and the right-side wall;

wherein the right-side, skin-engaging portion and the left-side, skin-engaging portion define a front gap distance that is smaller than a width of the back wall; and wherein the hemorrhoid treatment liquid outlet further comprises a spout on an end of the base portion distal the curved midsection wherein the spout has a downwardly facing lip.

2. The hemorrhoid treatment device for the treatment of hemorrhoids in a human of claim 1, wherein the downwardly facing lip has a perimeter edge that is curved along all of the perimeter edge.

3. The hemorrhoid treatment device for the treatment of hemorrhoids in a human of claim 2, wherein the front gap distance is the same or substantially the same along an entire height of the left-side wall and the right-side wall.

4. The hemorrhoid treatment device for the treatment of hemorrhoids in a human of claim 3, wherein a hemorrhoid treatment liquid is spaced within the hemorrhoid treatment device and the hemorrhoid treatment liquid is chosen from the group consisting of: water, and a combination or solution of water and sodium chloride, hydrocortisone, lidocaine, witch hazel, an essential oil, lavender oil, an analgesic, or mixtures thereof.

5. The hemorrhoid treatment device for the treatment of hemorrhoids in a human of claim 4, wherein the back wall width has a back wall width defined by the distance between the left-side wall and the right-side wall and the back wall width gradually decreases and tapers from the top edge to the bottom of the rear wall and wherein the elongated upper portion, exterior facing surface aligns with the curved section, exterior facing surface and the curved section, exterior facing surface aligns with the base portion, exterior-facing surface and wherein the left-side wall and the right-side wall have curved cross-sections in a same plane that is perpendicular to both of the left-side wall and the right-side wall.

6. The hemorrhoid treatment device for the treatment of hemorrhoids in a human of claim 5, wherein the hemorrhoid treatment device is a unitary device with all components integrally formed together to create the hemorrhoid treatment device.

7. The hemorrhoid treatment device for the treatment of hemorrhoids in a human of claim 1, wherein the front gap distance is the same or substantially the same along an entire height of the left-side wall and the right-side wall.

8. The hemorrhoid treatment device for the treatment of hemorrhoids in a human of claim 1, wherein a hemorrhoid treatment liquid is spaced within the hemorrhoid treatment device and the hemorrhoid treatment liquid is chosen from the group consisting of: water, and a combination or solution of water and sodium chloride, hydrocortisone, lidocaine, witch hazel, an essential oil, lavender oil, an analgesic, or mixtures thereof.

9. The hemorrhoid treatment device for the treatment of hemorrhoids in a human of claim 1, wherein the elongated upper portion, exterior facing surface aligns with the curved section, exterior facing surface and the curved section, exterior facing surface aligns with the base portion, exterior-facing surface and wherein the left-side wall and the right-side wall have curved cross-sections in a same plane that is perpendicular to both of the left-side wall and the right-side wall.

10. The hemorrhoid treatment device for the treatment of hemorrhoids in a human of claim 1, wherein the back wall width has a back wall width defined by the distance between the left-side wall and the right-side wall and the back wall width is greater at the top edge than at the bottom of the back wall.

11. The hemorrhoid treatment device for the treatment of hemorrhoids in a human of claim 1, wherein the back wall width and having a back wall width defined by the distance between the left-side wall and the right-side wall gradually decreases and tapers from the top edge to the bottom of the rear wall.

12. The hemorrhoid treatment device for the treatment of hemorrhoids in a human of claim 1, wherein the hemorrhoid treatment device is a unitary device with all components integrally formed together to create the hemorrhoid treatment device.

13. The hemorrhoid treatment device for the treatment of hemorrhoids in a human of claim 1, wherein the hemorrhoid treatment device is a unitary, integral device without any joints between the elongated upper portion, the curved midsection, and the base portion.

14. The hemorrhoid treatment device for the treatment of hemorrhoids in a human of claim 1 further comprising:

a handle having a handle main portion and a handle top edge and wherein the handle is engaged with the back wall and the handle top edge is substantially on the same plane as the top edge of the elongated upper portion of the hemorrhoid treatment device.

15. The hemorrhoid treatment device for the treatment of hemorrhoids in a human of claim 14 further comprising a left-side wall pair of ridges formed on the left-side wall and a right-side wall pair of ridges formed on the right-side wall wherein the left-side wall pair of ridges substantially mirror one another in shape and general dimension and are integrally formed on the left-side wall and wherein the right-side wall pair of ridges substantially mirror one another in shape and general dimension and are integrally formed on the right-side wall.

16. The hemorrhoid treatment device for the treatment of hemorrhoids in a human of claim 15 further comprising:

an extension bracket having:

a main bracket section having an extension bracket upper portion with an exterior surface that faces the exterior of the main bracket section and an interior surface that faces the interior of the main bracket section wherein the interior surface of the main bracket section has a horizontal bracket channel thereon; an extension bracket lower section interior surface; and a wherein the main bracket section of the extension bracket has an at least substantially similar cross-sectional shape as the elongated upper portion of the hemorrhoid treatment device;

a downward facing, hemorrhoid treatment device engaging projection extending downward from the main bracket section and having an interior facing side and an exterior facing side having a lateral extension configured to frictionally fit within and engage a horizontal groove on the elongated upper portion of the hemorrhoid treatment device when the extension bracket is engaged with the hemorrhoid treatment device; and an extension bracket attachment fin engaged with the main bracket section and extending rearwardly away from the main bracket section wherein the extension bracket attachment fin includes a planar fin section that aligns with the handle main portion when the extension bracket and the hemorrhoid treatment device are engaged with one another; and a downwardly facing u-shaped retainer having a downwardly facing channel that receives the handle top edge within it when the extension bracket and the hemorrhoid treatment device are engaged with one another, a left side pair of bracket ridges that align with the left-side wall pair of ridges when the when the extension bracket and the hemorrhoid treatment device are engaged with one another and a right side pair of bracket ridges located opposite the left side pair of bracket ridges that align with the right-side wall pair of ridges when the extension bracket and the hemorrhoid treatment device are engaged with one another and wherein the exterior surface of the main bracket section and an exterior surface of the elongated upper portion align with one another when the extension bracket and the hemorrhoid treatment device are engaged with one another.

17. The hemorrhoid treatment device for the treatment of hemorrhoids in a human of claim 1 further comprising a horizontal groove on the elongated upper portion, interior facing surface proximate the top edge of the elongated upper portion and wherein the right-side, skin-engaging portion of the right-side wall and the left-side, skin-engaging portion of the left-side wall do not touch one another and wherein the right-side, skin-engaging portion has a right-side, curvilinear cross-sectional shape and the left-side, skin-engaging portion has a left-side, curvilinear cross-sectional shape such that a terminal edge of the right-side, skin-engaging portion and a terminal edge of the left-side, skin-engaging portion face away from one another and form a smooth, curved surface along a length of the left-side wall and a length of the right-side wall that engages the skin of a human when the hemorrhoid treatment device is in a use position engaged to a human user.

18. The hemorrhoid treatment device for the treatment of hemorrhoids in a human of claim 1 further comprising:

a handle having a handle main portion and a handle top edge and wherein the handle is engaged with the back wall and the handle top edge is substantially on the same plane as the top edge of the elongated upper portion of the hemorrhoid treatment device;

a first extension bracket comprising:

a main bracket section having an extension bracket upper portion with an exterior surface that faces the exterior of the main bracket section and an interior surface that faces the interior of the main bracket section wherein the interior surface of the main bracket section has a horizontal bracket channel thereon; an extension bracket lower section interior surface; and a wherein the main bracket section of the first extension bracket has an at least substantially similar cross-sectional shape as the elongated upper portion of the hemorrhoid treatment device;

a downward facing, hemorrhoid treatment device engaging projection extending downward from the main bracket section and having an interior facing side and an exterior facing side having a lateral extension configured to frictionally fit within and engage a horizontal groove on the elongated upper portion of the hemorrhoid treatment device when the first extension bracket is engaged with the hemorrhoid treatment device; and an extension bracket attachment fin engaged with the main bracket section and extending rearwardly away from the main bracket section wherein the first extension bracket attachment fin includes a planar fin section that aligns with the handle main portion when the first extension bracket and the hemorrhoid treatment device are engaged with one another and a downwardly facing u-shaped retainer having a downwardly facing channel that receives the handle top edge within it when the first extension bracket and the hemorrhoid treatment device are engaged with one another.

19. A hemorrhoid treatment kit for the treatment of hemorrhoids in a human comprising:

a hemorrhoid treatment kit comprising a hemorrhoid treatment device and at least one extension bracket to optionally lengthen the hemorrhoid treatment device:

an elongated upper portion having a top edge defining a hemorrhoid treatment liquid receiving opening, an elongated upper portion, interior facing surface, and an elongated upper portion, exterior facing surface;

a base portion having a hemorrhoid treatment liquid outlet, a base portion, interior facing surface, and a base portion, exterior facing surface;

a curved midsection spaced between the elongated upper portion and the base portion having a curved section, interior-facing surface and a curved section, exterior facing surface;

wherein the base portion, the curved midsection, and the elongated upper portion, collectively form the hemorrhoid treatment device;

wherein the elongated upper portion, interior facing surface aligns with the curved section, interior facing surface; the curved section, interior facing surface aligns with the base portion, interior-facing surface; the elongated upper portion, exterior facing surface aligns with the curved section, exterior facing surface; and the curved section, exterior facing surface aligns with the base portion, exterior-facing surface; and wherein the hemorrhoid treatment device is configured to comprise:

a left-side wall having a left-side, human skin-engaging portion and a left-side, rear wall engaging portion on the opposite side of the left-side wall of the left-side, human skin-engaging portion;

a right-side wall having a right-side skin-engaging portion and a right-side, rear wall engaging portion opposite the right-side skin-engaging portion;

a back wall extending from the top edge to a back wall bottom portion wherein the back wall is interconnected with the left-side wall and the right-side wall;

wherein the right-side, skin-engaging portion and the left-side, skin-engaging portion define a front gap distance that is smaller than a width of the back wall; and a planar handle engaged with the back wall and having a handle top edge in the same or substantially in the same plane as a plane defined by the top edge of the elongated upper portion of the hemorrhoid treatment device; and wherein the at least one extension bracket includes:

a main bracket section having an extension bracket upper portion with an exterior surface that faces the exterior of the main bracket section and an interior surface that faces the interior of the main bracket section wherein the interior surface of the main bracket section has a horizontal bracket channel thereon; an extension bracket lower section interior surface; and a wherein the main bracket section of the at least one extension bracket has an at least substantially similar cross-sectional shape as the elongated upper portion of the hemorrhoid treatment device;

a downward facing, hemorrhoid treatment device engaging projection extending downward from the main bracket section and having an interior facing side and an exterior facing side having a lateral extension configured to frictionally fit within and engage a horizontal groove on the elongated upper portion of the hemorrhoid treatment device when the at least one extension bracket is engaged with the hemorrhoid treatment device; and an extension bracket attachment fin engaged with the main bracket section and extending rearwardly away from the main bracket section wherein the extension bracket attachment fin includes a planar fin section that aligns with a handle main portion when the at least one extension bracket and the hemorrhoid treatment device are engaged with one another; and a downwardly facing u-shaped retainer having a downwardly facing channel that receives the handle top edge within it when the at least one extension bracket and the hemorrhoid treatment device are engaged with one another, a left side pair of bracket ridges that align with a left-side wall pair of ridges formed ont the left-side wall when the at least one extension bracket and the hemorrhoid treatment device are engaged with one another and a right side pair of bracket ridges located opposite the left side pair of bracket ridges that align with a right-side wall pair of ridges formed on the right-side wall when the at least one extension bracket and the hemorrhoid treatment device are engaged with one another and wherein the exterior surface of the main bracket section and an exterior surface of the elongated upper portion align with one another when the at least one extension bracket and the hemorrhoid treatment device are engaged with one another.

20. A method of treating a user's hemorrhoids using a main hemorrhoid treatment device comprising the steps of:

while in a shower or under another supply of running water delivered from above a user's waist level, grasping a planar handle of a hemorrhoid treatment device for the treatment of hemorrhoids in a human comprising:

an elongated upper portion having a top edge defining a hemorrhoid treatment liquid receiving opening, an elongated upper portion, interior facing surface, and an elongated upper portion, exterior facing surface;

a base portion having a hemorrhoid treatment liquid outlet, a base portion, interior facing surface, and a base portion, exterior facing surface;

a curved midsection spaced between the elongated upper portion and the base portion having a curved section, interior-facing surface and a curved section, exterior facing surface;

wherein the base portion, the curved midsection, and the elongated upper portion, collectively form the hemorrhoid treatment device;

wherein the elongated upper portion, interior facing surface aligns with the curved section, interior facing surface; the curved section, interior facing surface aligns with the base portion, interior-facing surface; the elongated upper portion, exterior facing surface aligns with the curved section, exterior facing surface; and the curved section, exterior facing surface aligns with the base portion, exterior-facing surface;

wherein the hemorrhoid treatment device is configured to comprise:

a left-side wall having a left-side, human skin-engaging portion and a left-side, rear wall engaging portion on the opposite side of the left-side wall of the left-side, human skin-engaging portion;

a right-side wall having a right-side skin-engaging portion and a right-side, rear wall engaging portion opposite the right-side skin-engaging portion;

a back wall extending from the top edge to a back wall bottom portion wherein the back wall is interconnected with the left-side wall and the right-side wall;

wherein the right-side, skin-engaging portion and the left-side, skin-engaging portion define a front gap distance that is smaller than a width of the back wall;

the planar handle engaged with the back wall and having a handle top edge in the same or substantially in the same plane as a plane defined by the top edge of the elongated upper portion of the hemorrhoid treatment device; and a spout on an end of the base portion distal the curved midsection;

optionally adding a hemorrhoid treatment liquid chosen from the group consisting of: water, and a combination or solution of water and sodium chloride, hydrocortisone, lidocaine, witch hazel, an essential oil, lavender oil, an analgesic, or mixtures thereof into a space between the left-side wall and the right-side wall prior to use;

optionally frictionally fitting an extension bracket to the main hemorrhoid treatment device wherein engagement of the extension bracket into engagement with the main hemorrhoid treatment device is achieved by applying a finger force or other force of a human to either or both of the hemorrhoid treatment device and the extension bracket to temporarily flex them and, once the lateral extension rim of the extension bracket is in an aligned position with a groove of the main hemorrhoid treatment device, releasing them to allow a snap-fit engagement;

optionally frictionally fitting a second extension or more extension brackets to the extension bracket wherein engagement is achieved by applying a finger force or other force of a human to either or both of the first extension attachment or the second or more extension brackets to temporarily flex them, and one the lateral extension rim of the extension attachment aligns with a groove of the second or more extension brackets or the lateral extension rim of the second or more extension brackets aligns with the groove of the extension attachment, releasing them to allow the snap-fit engagement;

positioning the hemorrhoid treatment device between a user's buttocks and/or on the perineum and holding the hemorrhoid treatment device in position without the use of a user's hands;

delivering water from the shower or other water source to enter the hemorrhoid treatment liquid receiving opening of the hemorrhoid treatment device or a hemorrhoid treatment liquid receiving opening of an extension bracket;

allowing gravity to cause the water or a combination or solution of water and a component chosen from the group consisting of: sodium chloride, hydrocortisone, lidocaine, witch hazel, an essential oil, lavender oil, an analgesic, or mixtures thereof wash over the user's hemorrhoid or hemorrhoids for a period of time sufficient to pass through the interior of the hemorrhoid treatment device and over or otherwise into contact with and thereby treat the user's hemorrhoid or hemorrhoids while the user is standing in a position where water is provided from the shower or other water source; and dispensing the water or the combination or solution of water and the component from the hemorrhoid treatment device or the combined hemorrhoid treatment device and extension bracket system through the spout.

* * * * *